(12) United States Patent
Phillips

(10) Patent No.: US 7,513,871 B2
(45) Date of Patent: Apr. 7, 2009

(54) BLOOD FLOW ANALYSIS SYSTEM

(75) Inventor: Robert Allan Phillips, Coffs Harbour (AU)

(73) Assignee: USCOM Pty Ltd., Korora, New South Wales (AU)

( * ) Notice: Subject to any disclaimer, the term of this patent is extended or adjusted under 35 U.S.C. 154(b) by 48 days.

(21) Appl. No.: 10/523,051

(22) PCT Filed: Jul. 25, 2003

(86) PCT No.: PCT/AU03/00946

§ 371 (c)(1),
(2), (4) Date: Feb. 2, 2005

(87) PCT Pub. No.: WO2004/012618

PCT Pub. Date: Feb. 12, 2004

(65) Prior Publication Data

US 2005/0234339 A1    Oct. 20, 2005

(30) Foreign Application Priority Data

Aug. 6, 2002    (AU) ............................. 2002950611

(51) Int. Cl.
    A61B 8/02    (2006.01)
(52) U.S. Cl. .................. 600/454; 600/453; 600/457
(58) Field of Classification Search ............. 600/437, 600/443, 444, 453–459, 439, 300, 419, 440, 600/441, 504–505; 128/712; 381/17, 1, 381/63
See application file for complete search history.

(56) References Cited

U.S. PATENT DOCUMENTS

| | | | |
|---|---|---|---|
| 4,413,629 A | | 11/1983 | Durley, III et al. |
| 4,796,634 A | | 1/1989 | Huntsman et al. |
| 4,807,636 A | | 2/1989 | Skidmore et al. |
| 4,866,613 A | * | 9/1989 | Amemiya et al. ........... 600/454 |
| 5,447,164 A | * | 9/1995 | Shaya et al. ................. 600/523 |
| 5,546,943 A | * | 8/1996 | Gould ......................... 600/425 |
| 5,640,960 A | | 6/1997 | Jones et al. |
| 5,891,036 A | | 4/1999 | Izumi |
| 6,106,472 A | | 8/2000 | Chiang et al. |
| 6,149,587 A | * | 11/2000 | Raines ........................ 600/300 |
| 6,506,157 B1 | * | 1/2003 | Teigman et al. ............. 600/439 |
| 6,527,722 B1 | * | 3/2003 | Fazioli et al. ............... 600/457 |
| 6,530,887 B1 | * | 3/2003 | Gilbert et al. ............... 600/459 |
| 6,569,101 B2 | * | 5/2003 | Quistgaard et al. .......... 600/523 |
| 2002/0091319 A1 | | 7/2002 | Moehring et al. |

FOREIGN PATENT DOCUMENTS

| | | |
|---|---|---|
| EP | 0 706 777 A2 | 4/1996 |
| WO | 96/32888 | 10/1996 |

* cited by examiner

Primary Examiner—Eric F Winakur
Assistant Examiner—Lawrence N Laryea
(74) Attorney, Agent, or Firm—Merchant & Gould P.C.

(57) ABSTRACT

A portable apparatus for conveying blood flow parameters to a user, the apparatus comprising: a transducer device for providing for Doppler monitoring of flows within a patient; a processing unit interconnected to the transducer unit and adapted to extract a blood flow signal from the operation of the transducer and process the blood flow signal so as to produce a video blood flow signal and an audio blood flow signal; a display unit interconnect to the processing unit for visualising the video blood flow signal; and at least one audio emission devices interconnected to the processing unit for emission of the audio blood flow signal to the ears of the user.

10 Claims, 5 Drawing Sheets

BLOOD FLOW ANALYSIS SYSTEM

FIELD OF THE INVENTION

The present invention relates to the field of Doppler flow measurements of blood flow and, in particular, discloses a hand-held device, hereinafter called an "Echoscope" having functionality similar to that of an augmented stethoscope but further including visualisation and audiospatialisation capabilities.

BACKGROUND OF THE INVENTION

The operational characteristics of blood flow through the body has been an important parameter in medical studies for many years. Traditionally, stethoscopes have been used by medical professionals to listen to blood flows within the body in order to determine irregular characteristics. Further, the taking of blood pressure has traditionally relied upon monitoring blood flow utilising stethoscope devices to listen to the onset of flows.

Unfortunately, standard stethoscope techniques rely on simple mechanical transmission of audio information to the ears of a user which provide only limited information to the medical specialist. It would be desirable to provide for a more informative system of providing information on blood flows within the body to the medical specialist.

SUMMARY OF THE INVENTION

It is an object of the present invention to provide for an improved form of diagnostic monitoring of blood flows within the body including cardiac blood flow measurement.

In accordance with a first aspect of the present invention there is provided a portable apparatus for conveying blood flow parameters to a user, the apparatus comprising: a transducer device for providing for Doppler monitoring of flows within a patient; a processing unit interconnected to the transducer unit and adapted to extract a blood flow signal from the operation of the transducer and process the blood flow signal so as to produce a video blood flow signal and an audio blood flow signal; a display unit interconnect to the processing unit for visualising the video blood flow signal; and at least one audio emission devices interconnected to the processing unit for emission of the audio blood flow signal to the ears of the user.

Preferably, the processing unit and the display unit are packaged as a handheld device and the processing unit performs audio spatialisation of the audio blood flow signal and the number of audio emission devices is at least two. Preferably, the audio spatialisation includes a spatial separation of information in accordance with the depth from a transducer element.

In accordance with a first aspect of the present invention there is provided a method of transmission of information of blood flow characteristics within a patient, the method comprising the steps of (a) providing a Doppler flow signal indicative of blood flows within the body, (b) visualising the Doppler flow signal on a display device; and (c) simultaneously providing an audio output to the listener of the Doppler blood flow signal.

Preferably the step (c) includes providing an apparent spatialisation of the audio output to the listener.

The method can also including simultaneously recording the Doppler flow signal and related information for later analysis.

BRIEF DESCRIPTION OF THE DRAWINGS

The preferred and other embodiments of the present invention will now be described with reference to the accompanying drawings in which.

DESCRIPTION OF PREFERRED AND OTHER EMBODIMENTS

In the preferred embodiment, there is provided a stethoscope substitute, hereinafter called an "Echoscope". The Echoscope utilises a continuous wave Doppler beam to measure and image blood flows within the body. Further, the Echoscope also includes auralisation of the resultant measurements so as to provide for advanced stethoscope-type activities. Preferably, spatialisation of the audio is also provided.

Figure 1:
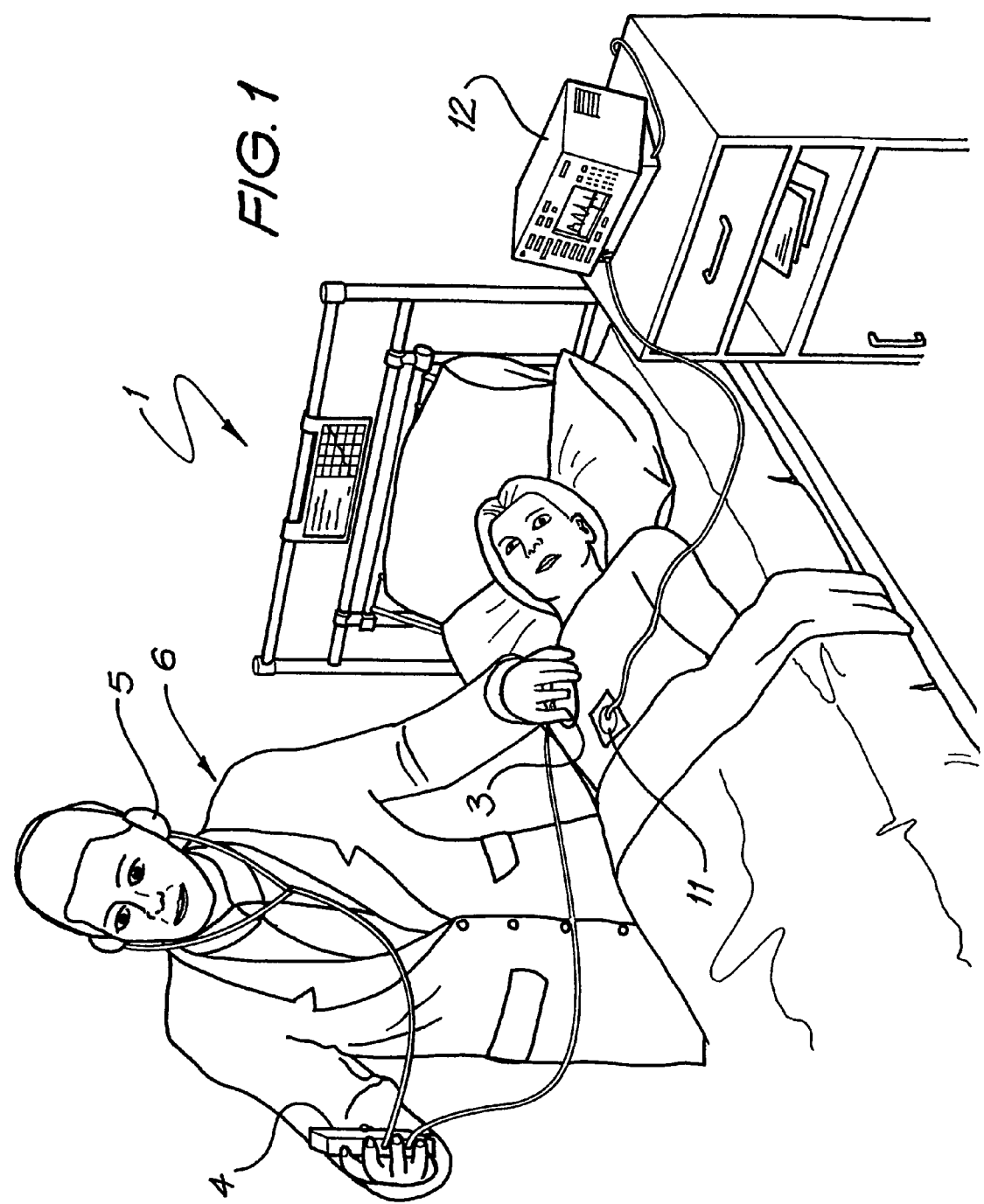
FIG. 1 illustrates an operational environment of the preferred embodiment.

Turning now to FIG. 1, there is illustrated an example of the operational environment of the preferred embodiment. In this example, a patient 2 is presented in a hospital-type environment. The patient 2 has a number of predetermined monitoring devices e.g. 11, 12 monitoring his physiological condition.

The Echoscope device is designed to be utilised by a physician 6 so as to gain information about the operation of the internal portions of blood flow within the body of patient 2. The Echoscope device includes an interconnected hand-held transducer 3, a processing and display unit 4 and a set of headphones 5. The Echoscope is designed to utilise continuous wave (CW) Doppler processing techniques so as to process an ultrasound signal emitted by a transducer 3 so as to produce corresponding blood flow indicator information which is displayed on device 4 and aurally output via headphones 5.

Figure 2:
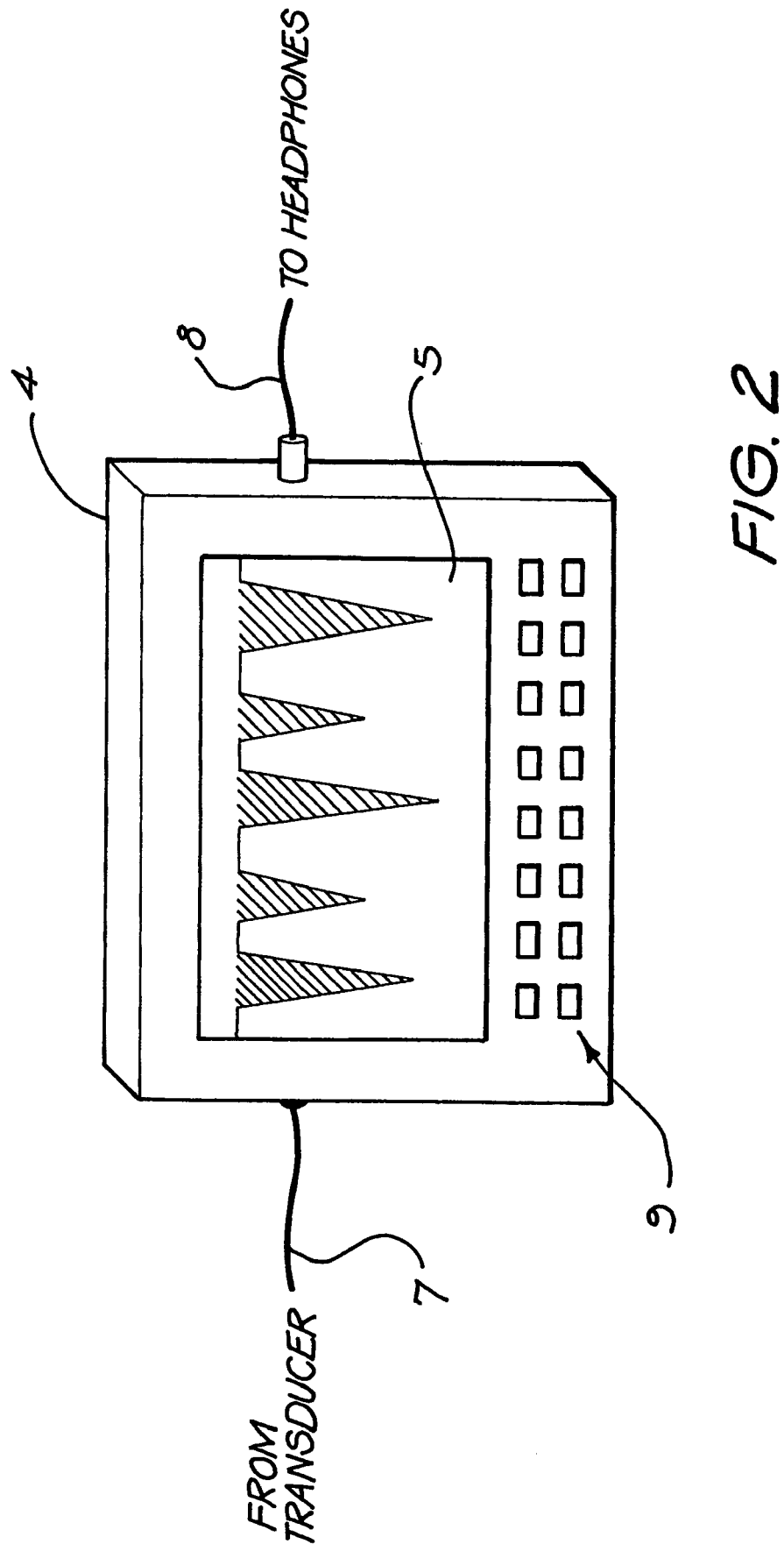
FIG. 2 illustrates the processing and display unit of the preferred embodiment.

Turning now to FIG. 2, there is illustrated an enlarged view of the processing and display unit 4. The processing and display unit interacts with input/output signals 7 which are transmitted and received from the transducer device. At the output 8, an audio signal is output to the headphone devices. The arrangement 4 includes a display 5 which displays information relating to the signal received by transducer 7. The display 5 and audio output is influenced by a series of control buttons e.g. 8 which control the information on the display.

The preferred embodiment utilises continuous wave (CW) Doppler to monitor is the blood flow. The CW Doppler is a non-invasive technique in which ultrasonic signals from the transducer element are directed into a blood carrying vessel of a patient. Doppler shifts in the reflected signal provide an indication of the rate of blood flow. The principles of the CW Doppler flow measurement are known. For example, Patent Co-operation Treaty (PCT) Publication No. WO99/66835 entitled "Ultrasonic Cardiac Output Monitor" describes in more detail an ultrasonic transducer device suitable for measuring blood flow using the CW Doppler method. The contents of the aforementioned specification are hereby included by cross-reference.

Figure 3:
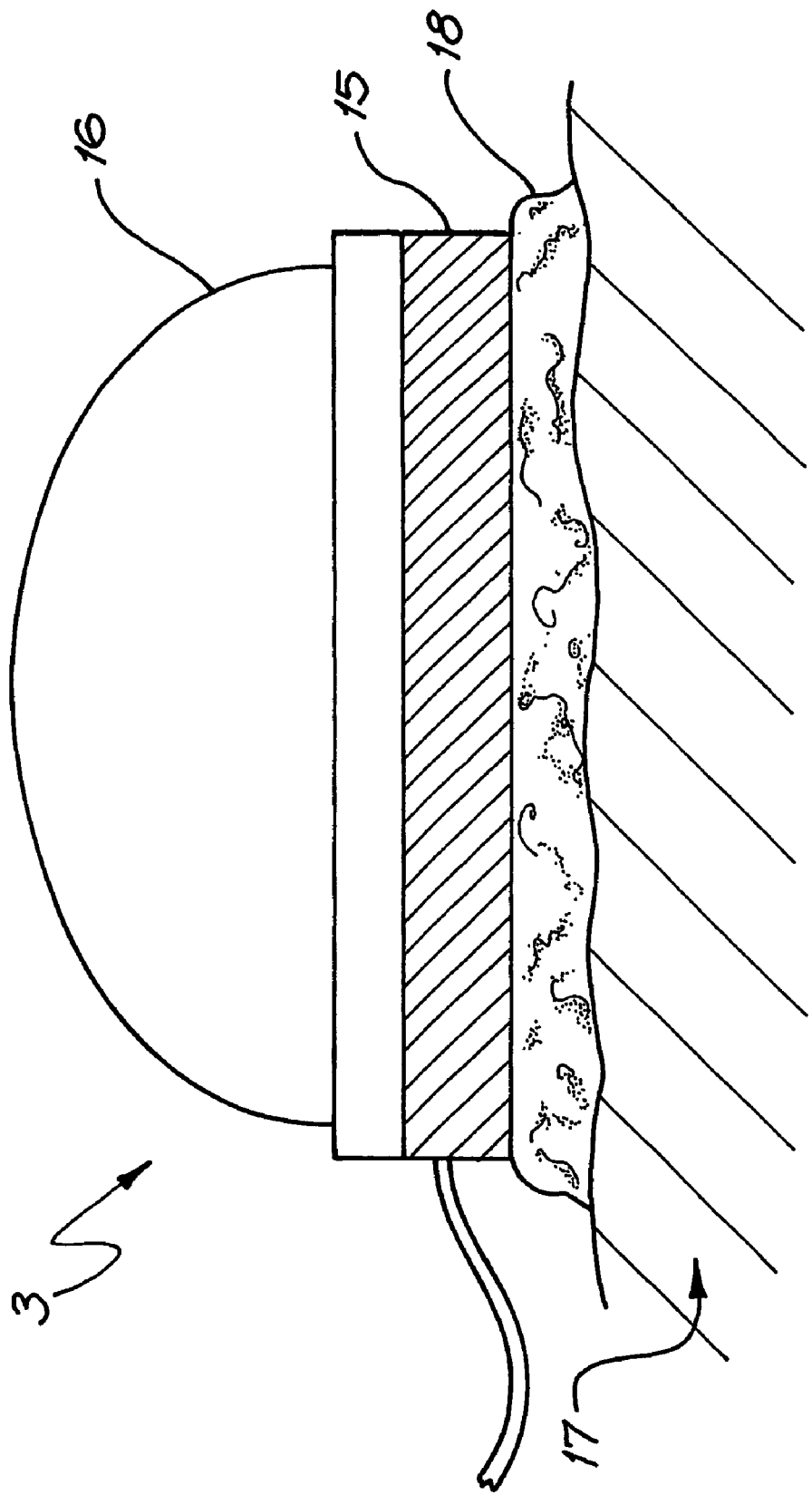
FIG. 3 illustrates a transducer device suitable for utilisation with the preferred embodiment.

Turning now to FIG. 3, there is illustrated an enlarged view of one form of the transducer element 3. The transducer element 3 includes an ultrasonic transducer 15 attached to a positioning device 16 which can be utilised to set the position of the transducer. Between the transducer 15 and a patient's skin 17, is placed a gel coupling layer 18 for coupling the ultrasonic transducer vibrations to the skin 17.

Figure 4:
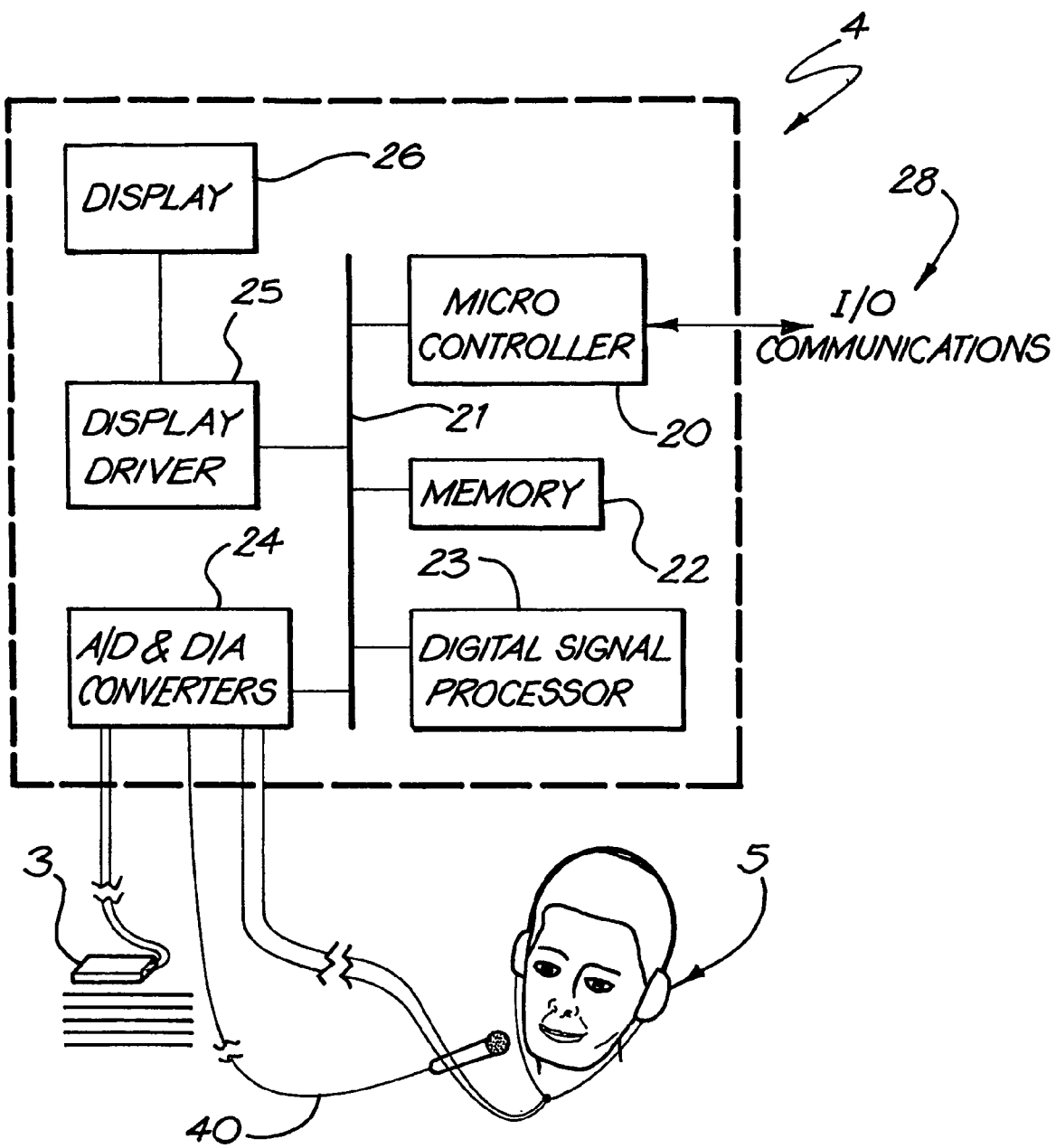
FIG. 4 illustrates schematically a functional block diagram of the hardware portions of the preferred embodiment.

Turning now to FIG. 4, there is illustrated a schematic arrangement of the functional hardware of the processing and display unit 4. The arrangement of FIG. 4 illustrates merely one example hardware structure of the processing and display unit 4 and it will be obvious to those skilled in the field of construction of complex hardware devices that other arrangements are possible. For example, fully custom applications specific integrated circuit (ASIC) technology could be utilised to reduce the number of overall components of the unit 4. In any event, one arrangement can be based around a micro-controller 20 which has overall control of the unit 4. The micro-controller 20 communicates with other devices over a bus 21. Devices attached to the bus include a memory unit 22, a DSP unit 23, A to D and D to A converters 24 and a display driver 25 which interacts with the display 26. The micro-controller 20 is also preferably able to communicate with a series of other devices via an input/output communication port 28. The A to D converters 24 are responsible for controlling the transducer device 3 and headphones 5. The whole system 4 operates under the control of micro-controller 20 which runs programs stored in memory 22 with the DSP 23 performing real time signal processing operations in the normal manner.

Figure 5:
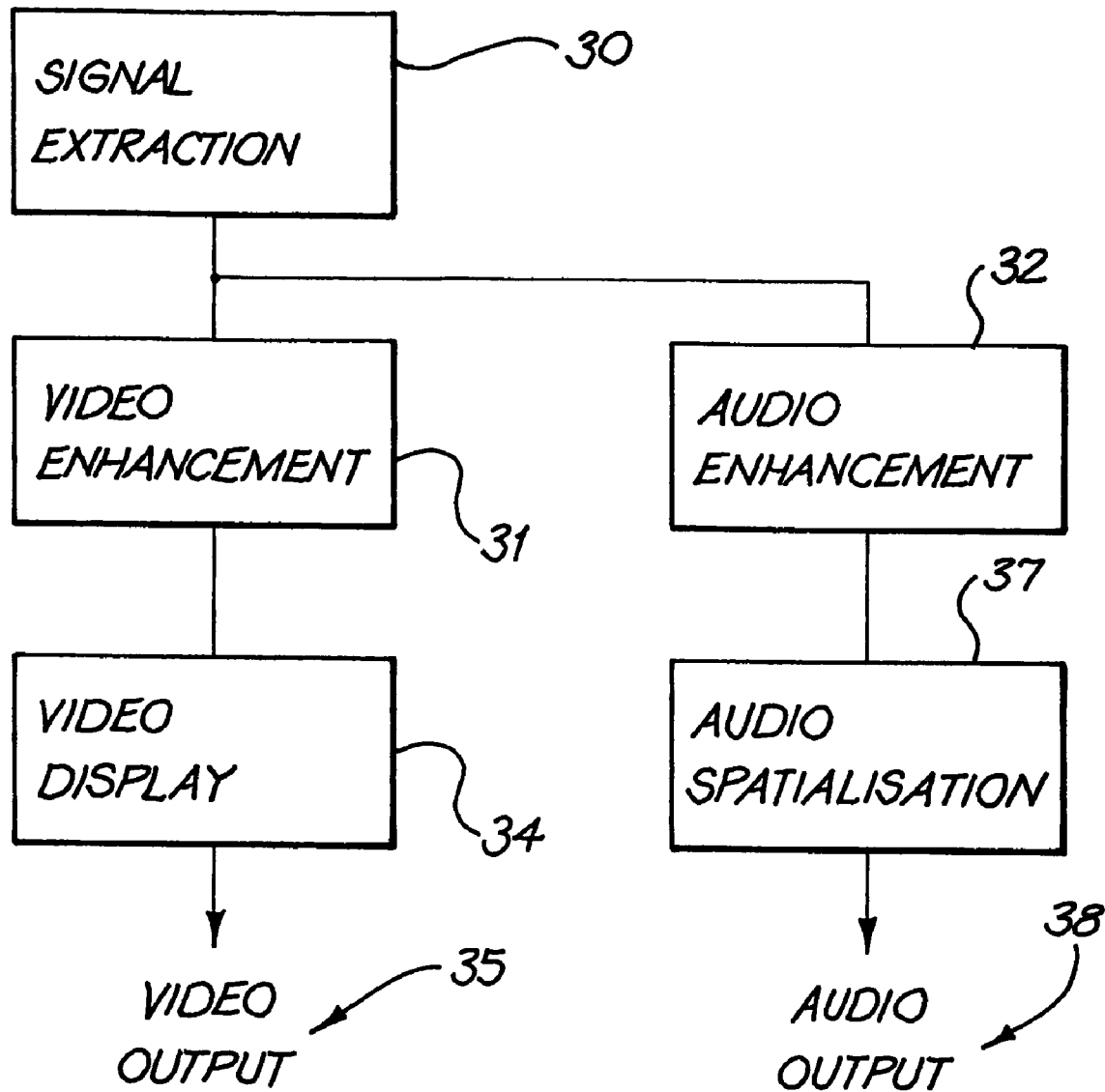
FIG. 5 illustrates a functional block diagram of the software processing of the preferred embodiment.

Turning now to FIG. 5, there is illustrated the core overall portions of one possible software system of the preferred embodiment. In this arrangement, the signal received from the transducer is extracted 30 and subjected to video and audio enhancement processing 31, 32. The video enhancement can include standard image processing routines to enhance and display the received signal in accordance with external control settings. The output signal is then processed for display 34 before being output 35. The audio signal is enhanced 32 utilising standard techniques such as noise cancelling or the like. Optionally, the output audio signal can also be spatialised around a listener. The spatialisation process can provide for depth cues of the audio signal received by the physician. Many different forms of spatialisation can be performed from the simple to the complex. In a simple technique, the left and right channel outputs can be manipulated in accordance with the depth of the signal received so as to produce a panning of the signal from the left ear to the right ear depending on the transducer delay monitored. Other methods can include the full binaualisation of the audio signal so as to spatialise portions of the signal around the listener. The binauralisation process is well known to those skilled in the art of audio digital signal processing and suitable techniques for spatialisation of the audio around listener are disclosed in PCT publication No. WO99/49574 entitled "Audio Signal Processing Method and Apparatus", the contents of which are hereby incorporated by cross-reference.

The audio signal can then be output 38 to the headphones.

Many other refinements are possible. For example, the information or signal parameters recorded by the physician can be stored for later download in addition to the case notes associated with the case. A microphone 40 can be optionally provided for recording and storing the physicians notes Further, continual audio and video enhancements can be made and up-loaded to the system. Also, depending on the mode settings of the device, the audio and visual signal processing can be undertaken to highlight certain detected anomalous aspects of the received signals. For example, a speed control could be provided so that particular portions of the audio signal are played at half speed etcetera.

Further modifications, obvious to those skilled in the art of advanced hardware/software design and medical instrumentation can be made thereto without departing from the scope of the present invention.

The claims defining the invention are as follows:

1. A portable apparatus for conveying blood flow parameters to a user, the apparatus comprising:
    a transducer device for providing for a Continuous Wave (CW) Doppler monitoring of blood flows within a patient;
    a processing unit interconnected to said transducer unit and adapted to extract a blood flow signal from the operation of said transducer and process said blood flow signal so as to produce a video blood flow signal and an audio blood flow signal;
    a display unit interconnect to said processing unit for visualising the video blood flow signal;
    wherein said processing unit performs audio spatialisation of said audio blood flow signal to provide a spatialised audio blood flow signal; wherein said audio spatialisation includes spatial separation of information in accordance with the depth of the received signal from said transducer device;
    and at least two audio emission devices interconnected to said processing unit for emission of an audible form of said spatialised audio blood flow signal to the ears of said user.

2. An apparatus as claimed in claim 1 wherein said processing unit and said display unit are packaged as a handheld device.

3. An apparatus as claimed in claim 1, wherein said processing unit performs substantially real-time audio spatialisation of said audio blood flow signal.

4. An apparatus as claimed in claim 1 further comprising: storage means for storing information associated with subjects on whom the apparatus is used.

5. An apparatus as claimed in claim 4 further comprising: a microphone for use in recording audio commentary by the user for storage in said storage means.

6. A method of transmission of information of blood flow characteristics within a patient to a user, the method comprising the steps of
    (a) providing a Continuous Wave (CW) Doppler flow signal indicative of blood flows within the body,
    (b) visualising the Continuous Wave (CW) Doppler flow signal on a display device; and
    (c) simultaneously providing an audible form of a spatialised audio signal through at least one two audio emission devices to the ears of said user; wherein said spatialised audio blood flow signal is indicative of the of the depth of blood flowing associated with said provided Continuous Wave (CW) Doppler blood flow signal received from a transducer device.

7. A method as claimed in claim 6 wherein said step (c) includes providing an apparent spatialisation of said audio output to said user.

8. A method as claimed in claim 6, wherein said audible form of said spatialised audio signal is substantially provided in real-time.

9. A portable apparatus for conveying blood flow parameters to a user, the apparatus comprising:
    a transducer device for providing for a Continuous Wave (CW) Doppler monitoring of blood flows within a patient;

a processing unit interconnected to said transducer unit and adapted to extract a blood flow signal from the operation of said transducer, to process said blood flow signal so as to produce a video blood flow signal and an audio blood flow signal, and to perform substantially real-time audio spatialisation of said audio blood flow signal to produce a spatialised audio blood flow signal;

a display unit interconnect to said processing unit for visualising the video blood flow signal; and at least two audio emission devices interconnected to said processing unit for emission of said spatialised audio blood flow signal to the ears of said user.

10. A method of transmission of information of blood flow characteristics within a patient to a user, the method comprising the steps of:
  (a) providing a Continuous Wave (CW) Doppler flow signal indicative of blood flows within the body,
  (b) visualising the Continuous Wave (CW) Doppler flow signal on a display device; and
  (c) simultaneously providing a substantially real-time spatialised audio output to said user, wherein said audio output is indicative of the Continuous Wave (CW) Doppler blood flow signal.

* * * * *